United States Patent [19]

Large et al.

[11] 4,115,409

[45] Sep. 19, 1978

[54] ALKANOLAMINE DERIVATIVES

[75] Inventors: Michael Stewart Large; Leslie Harold Smith, both of Macclesfield, England

[73] Assignee: Imperial Chemical Industries Limited, London, England

[21] Appl. No.: 745,162

[22] Filed: Nov. 26, 1976

[30] Foreign Application Priority Data

Dec. 5, 1975 [GB] United Kingdom ............... 50039/75

[51] Int. Cl.² .................. C07D 307/54; C07D 333/24
[52] U.S. Cl. .................................. 260/347.3; 544/35; 544/134; 260/287 R; 548/330; 548/342; 260/295 AM; 548/378; 260/298; 260/302 R; 260/302 H; 260/304 R; 260/304 D; 260/307 R; 260/307 H; 260/315; 260/326.1; 260/326.14 R; 260/326.4; 260/327 R; 260/330.5; 260/332.2 R; 260/332.2 A; 260/340.3; 260/345.5; 260/345.7 R; 260/346.73; 260/347.2; 260/465 D; 260/501.17; 260/501.19; 260/553 A; 260/556 R; 260/556 AR; 260/559 A; 260/559 T; 424/275; 424/285

[58] Field of Search ................. 260/332.2 R, 332.2 A, 260/347.2, 347.3; 424/278, 285

[56] References Cited

U.S. PATENT DOCUMENTS

| 2,776,991 | 1/1957 | Surrey ....................... 260/332.2 A X |
| 3,793,365 | 2/1974 | Winter et al. .......................... 560/39 |
| 3,933,911 | 1/1976 | Main ................................ 260/562 N |
| 3,944,611 | 3/1976 | Smith ............................... 260/562 R |
| 3,957,870 | 5/1976 | Main ................................ 260/562 N |
| 4,034,106 | 7/1977 | Smith ..................................... 424/304 |
| 4,034,112 | 7/1977 | Smith ..................................... 424/321 |

*Primary Examiner*—Richard L. Raymond
*Attorney, Agent, or Firm*—Cushman, Darby & Cushman

[57] ABSTRACT

Novel 1-aryloxy-3-carbamoylalkylamino-2-propanol derivatives, processes for their manufacture, pharmaceutical compositions containing them and methods of using them in the treatment of heart diseases. The compounds possess $\beta$-adrenergic blocking activity. Representative of the compounds disclosed is 1-(2-cyanophenoxy)-3-$\beta$-(N-2-furfurylcarbamoyl)ethylamino-2-propanol.

6 Claims, No Drawings

ALKANOLAMINE DERIVATIVES

This invention relates to new alkanolamine derivatives which possess β-adrenergic blocking activity. The invention is a modification of that claimed in U.K. Application No. 57970/72.

According to the invention there is provided a new alkanolamine derivative of the formula:

R—OCH$_2$.CHOH.CH$_2$NH—A—CO—NH—Y—R$^1$ wherein A stands for an alkylene radical of up to 12 carbon atoms; wherein Y stands for a direct link, or for an alkylene radical of up to 6 carbon atoms or an alkyleneoxy radical of from 2 to 6 carbon atoms; and wherein R stands for a heterocyclic radical or for an aryl radical of the formula:

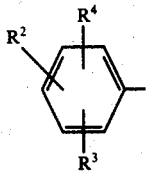

and R$^1$ stands for a heterocyclic radical or for an aryl radical of the formula:

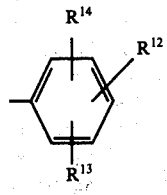

or for the hydrogen atom or for an alkyl, halogenoalkyl, alkenyl or cycloalkyl radical each of up to 10 carbon atoms; wherein R$^2$, R$^3$, R$^{12}$ and R$^{13}$, which may be the same or different, each stands for a hydrogen or halogen atom, a hydroxy, amino, nitro or cyano radical, an alkyl, hydroxyalkyl, cycloalkyl, alkenyl, alkynyl, alkoxy, alkylthio, cycloalkoxy, alkenyloxy, alkynyloxy or alkanoyl radical each of up to 6 carbon atoms, or an aryl, aryloxy or dialkylamino radical each of up to 12 carbon atoms; or wherein R$^2$ and R$^3$ together, and/or R$^{12}$ and R$^{13}$ together, form the trimethylene, tetramethylene, 1-oxotetramethylene, propenylene, but-2-enylene or buta-1,3-dienylene radical such that together with the adjacent benzene ring they form respectively the indanyl, 5,6,7,8-tetrahydronaphthyl, 5-oxo-5,6,7,8-tetrahydronaphthyl indenyl, 5,8-dihydronaphthyl or naphthyl radical; wherein R$^4$ and R$^{14}$, which may be the same or different, each stands for the hydrogen atom or for an amidic radical of the formula:

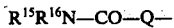
R$^{15}$R$^{16}$N—CO—Q—

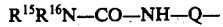
R$^{15}$R$^{16}$N—CO—NH—Q—

R$^{15}$R$^{16}$N—CO—Q$^1$—O— or

R$^{16}$—X—NR$^{15}$—Q— wherein X stands for the carbonyl or sulphonyl radical, wherein Q stands for a direct link or for an alkylene or alkenylene radical each of up to 6 carbon atoms; wherein Q$^1$ stands for an alkylene radical of up to 6 carbon atoms; wherein R$^{15}$ stands for the hydrogen atom or for an alkyl radical of up to 6 carbon atoms; wherein R$^{16}$ stands for the hydrogen atom, or for an alkenyl, cycloalkyl, hydroxyalkyl or alkoxyalkyl radical each of up to 6 carbon atoms, or for an alkyl, aryl, aralkyl or aralkenyl radical each of up to 10 carbon atoms; provided that when neither of R and R$^1$ is a heterocyclic radical the alkylene radical A separates the imino and carbonyl radicals by at least 2 carbon atoms; or an acid-addition salt thereof.

It will be observed that the alkanolamine derivative of the invention possesses an asymmetric carbon atom, namely the carbon atom of the —CHOH— group in the alkanolamine side-chain, and it can therefore exist in racemic and optically-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the "S" absolute configuration of the said —CHOH— group.

A suitable value for the alkylene radical A is, for example, the ethylene, trimethylene, tetramethylene, hexamethylene, dodecamethylene, 1-methylethylene, 2-methylethylene or 1,1-dimethylethylene radical. A is preferably the ethylene, trimethylene, 1-methylethylene or 1,1-dimethylethylene radical.

A suitable value for Y when it stands for an alkylene or alkyleneoxy radical is, for example, the methylene, ethylene, ethyleneoxy, trimethyleneoxy, 1-methylethylideneoxy or 1-methylpropylideneoxy radical.

A suitable value for R or R$^1$ when it stands for a heterocyclic radical is, for example, a mono-, bi- or tri-cyclic heterocyclic radical in which at least one ring is a 5- or 6-membered saturated or unsaturated hetero-ring containing one, two or three heteroatoms selected from nitrogen, oxygen and sulphur atoms; and in which the second and/or third ring, if present, may be a hetero-ring as defined above or may be a benzene ring, and which heterocyclic radical may optionally contain one or more substituents selected from halogen atoms, for example chlorine and bromine atoms, alkyl, alkoxy, acylamino, carbamoyl and alkanoyl radicals each of up to 6 carbon atoms, for example methyl, ethyl, methoxy, ethoxy, acetamido, methylcarbamoyl and acetyl radicals, aryl and aryloxy radicals each of up to 10 carbon atoms, for example phenyl, p-chlorophenyl and phenoxy radicals, and amino and substituted amino radicals, for example amino, alkylamino, dialkylamino and heterocyclic amino radicals each of up to 6 carbon atoms, for example amino, methylamino, dimethylamino and morpholino radicals; and, where the heterocyclic radical bears an appropriate degree of saturation, which heterocylic radical may optionally bear one or two oxo substituents.

A particular heterocyclic radical is, for example, a pyrrolyl, furyl, thienyl, imidazolyl, pyrazolyl, oxazolyl, isoxazolyl, thiazolyl, thiadiazolyl, pyridyl, pyranyl, pyrazinyl, pyridazinyl, pyrimidinyl, indolyl, isoindolyl, benzofuranyl, benzothienyl, benzimidazolyl, benzo-thiazolyl, benzothiadiazolyl, quinolyl, chromanyl, chromenyl, thiochromanyl, benzodioxanyl, carbazolyl or phenothiazinyl radical, for example the 2-pyrrolyl, 2-furyl, 2-thienyl, 3-thienyl, 2-imidazolyl, 5-methyl-3-pyrazolyl, 2-phenyl-5-methyl-3-pyrazolyl, 2-oxazolyl, 3-isoxazolyl, 2-thiazolyl, 2-p-chlorophenyl-4-thiazolyl, 4-morpholino-1,2,5-thiadiazol-3-yl, 4-pyridyl, 2-methyl-4-oxo-4H-pyran-3-yl, 3-methyl-2-pyrazinyl, 3-phenyl-2-pyrazinyl, 3-pyridazinyl, 2-p-chlorophenyl-6-methoxypyrimidin-4-yl, 2-indolyl, 3-indolyl, 4-indolyl, 2-methylindol-4-yl, 2,3-dihydro-2-oxo-4-indolyl, 3-oxo-2-phenylisoindolin-1-yl, 4-benzo[b]furanyl, 2,3-dihydro-4-benzo[b]-furanyl, 2,3-dimethyl-4-benzo[b]furanyl, 2-acetyl-7-benzo[b]-furanyl, 4-benz[b]thienyl, 2-benzimidazolyl, 5-benzothiazolyl, 5-(benzo[c]-[1,2,5]-thiadiazolyl), 2-quinolyl, 1,2-dihydro-2-oxo-5-quinolinyl, 1,4-dihydro-6-methoxy-4-oxo-2-quinolinyl, 1,2,3,4-tetrahydro-2-oxo-5-quinolinyl, 4-oxochroman-8-yl, 4-methyl-2-oxo-2H-chromen-8-yl, thiochroman-8-yl, 1,4-benzodioxan-5-yl, 1-carbazolyl or 1-phenothiazinyl radical.

A suitable value for $R^1$ when it stands for an alkyl, halogenoalkyl, alkenyl or cycloalkyl radical is, for example, the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, hydroxyalkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, hydroxymethyl, 1-hydroxyethyl, cyclopropyl, cyclopentyl, allyl, ethynyl, methoxy, isopropoxy, methylthio, cyclopentyloxy, allyloxy, propargyloxy, formyl or acetyl radical.

A suitable value for $R^2$, $R^3$, $R^{12}$ or $R^{13}$ when it stands for an aryl, aryloxy or dialkylamino radical is, for example, the phenyl, phenoxy or dimethylamino radical.

A suitable value for Q or $Q^1$ when it stands for an alkylene radical is, for example, the methylene, ethylene, trimethylene, ethylidene or 1-methylethylene radical. A suitable value for Q when it stands for an alkenylene radical is, for example, the vinylene radical.

A suitable value for $R^{15}$ when it stands for an alkyl radical is, for example, the methyl radical.

A suitable value for $R^{16}$ is, for example, the hydrogen atom or the allyl, cyclopropyl, cyclopentyl, cyclohexyl, 2-hydroxyethyl, 3-hydroxypropyl, 2-hydroxy-1-methylethyl, 2-hydroxy-1,1-dimethylethyl, β-methoxyethyl, methyl, ethyl, n-propyl, isopropyl, n-butyl, t-butyl, n-pentyl, n-hexyl, n-nonyl, phenyl, p-tolyl, p-chlorophenyl, benzyl or styryl radical.

A particular value for $R^4$ or $R^{14}$ when it stands for an amidic radical is, for example, the acetamido, propionamido, methanesulphonamido, carbamoyl, carbamoylmethyl, acetamidomethyl, 3-methylureido, 3-n-butylureido, carbamoylmethoxy, N-methylcarbamoylmethoxy or N-β-hydroxyethylcarbamoylmethoxy radical. The amidic substituent $R^4$ when present is preferably in the ortho- position of the benzene ring, and the amidic substituent $R^{14}$ when present is preferably in the para- position of the benzene ring.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

A preferred alkanolamine derivative of the invention is a compound of the formula given above wherein A stands for the ethylene, trimethylene, 1-methylethylene or 1,1-dimethylethylene radical; wherein R stands for a phenyl radical, $R^2$ is in the 2-position of the phenyl nucleus and is a hydrogen atom or a chloro or cyano radical, or an alkyl or alkoxy radical each of up to 3 carbon atoms and $R^3$ and $R^4$ both stand for hydrogen, or R stands for the unsubstituted naphthyl radical, or R stands for a bicyclic heterocyclic radical which is a benzene ring to which is fused a 5- or 6-membered saturated or unsaturated hetero-ring containing one or two hetero-atoms selected from nitrogen, oxygen and sulphur atoms, and to which benzene ring is attached, at a position adjacent to a fusion position of the hetero ring, the rest of the alkanolamine molecule; wherein $R^1$ stands for a hydrogen atom or for an alkyl or cycloalkyl radical each of up to 6 carbon atoms, or for the unsubstituted phenyl radical, or for a monocyclic, 5- or 6-membered, heterocyclic radical which contains one nitrogen, oxygen or sulphur atom as heteroatom; and wherein Y stands for a direct link, or for an alkylene radical of up to 3 carbon atoms, or for an alkyleneoxy radical of 2 to 4 carbon atoms; or is an acid-addition salt thereof.

One particularly preferred alkanolamine derivative of the invention is a compound of the formula given above wherein A stands for the ethylene radical, R stands for a phenyl radical and $R^2$, $R^3$ and $R^4$ have the meanings stated in the last paragraph, or R stands for the unsubstituted 1-naphthyl radical, $R^1$ stands for the 2-furyl radical and Y stands for the methylene radical, or is an acid-addition salt thereof.

A second particularly preferred alkanolamine derivative of the invention is a compound of the formula given above wherein A stands for the ethylene radical, R stands for a phenyl radical and $R^2$, $R^3$ and $R^4$ have the meanings stated in the last paragraph, or R stands for the benzo[b]fur-4-yl, benzo[b]thien-4-yl, 2,3-dihydrobenzo[b]fur-4-yl or 1,4-benzodioxan-5-yl radical, and either $R^1$ stands for the hydrogen atom or for an alkyl radical of up to 4 carbon atoms and Y stands for a direct link, or $R^1$ stands for the unsubstituted phenyl or tetrahydropyran-2-yl or for a pyridyl radical and Y stands for the methylene radical, or is an acid-addition salt thereof.

Specific alkanolamine derivatives of the invention are those hereinafter described in the Examples. Of these, preferred compounds by virtue of their high cardioselective β-adrenergic blocking activity (as hereinafter defined) are 1-phenoxy-, 1-(2-cyanophenoxy)-, 1-(2-chlorophenoxy)-, 1-(2-tolyloxy)- and 1-(2-methoxyphenoxy)-3-β-(N-2-furfurylcarbamoyl)ethylamino-2-propanol; 1-(1,4-benzodioxan-5-yloxy)-3-β-(N-isopropylcarbamoyl) and 3-β-(N-benzylcarbamoyl)ethylamino-2-propanol; and 1-benzo[b]fur-4-yloxy- and 1-benzo[b]thien-4-yloxy-3-β-(N-benzylcarbamoyl)ethylamino-2-propanol and the acid-addition salts thereof.

The alkanolamine derivative of the invention may be manufactured by any chemical process publically-known to be useful for the manufacture of chemically-analogous compounds.

According to a further feature of the invention there is provided a process for the manufacture of the alkanolamine derivative of the invention which comprises assembling in sequence, by chemical methods known to be useful for this purpose, the five radicals:

(i) an aryloxy radical of the formula:

R—O— wherein R has the meaning stated above;

(ii) an oxygenated three carbon radical of the formula:

$$-CH_2 . \overset{OR^5}{\underset{|}{CH}} . CH_2-$$

wherein $R^5$ stands for hydrogen or for a protecting group;

(iii) an imino radical of the formula —$NR^6$—, wherein $R^6$ stands for hydrogen or for a protecting group;

(iv) a radical of the formula:

—A—CO— wherein A has the meaning stated above; and (v) a radical of the formula:

—$NR^7$—Y—$R^1$ wherein $R^1$ and Y have the meanings stated above and wherein $R^7$ stands for hydrogen or for a protecting group; whereafter if one or more of $R^5$, $R^6$ and $R^7$ stands for a protecting group, the one or more protecting groups are removed.

The various stages of the assembly may be carried out in any possible order. Thus, for example:

(a) a phenolic compound of the formula:

R—OH wherein R has the meaning stated above, may first be reacted with an oxygenated three-carbon derivative, for example a compound of the formula:

$$\underset{CH_2}{\overset{O}{\diagup\diagdown}}CH . CH_2Z^2 \text{ or } Z^1CH_2 . \overset{OR^5}{\underset{|}{CH}} . CH_2Z^2$$

wherein $R^5$ has the meaning stated above, wherein $Z^1$ stands for a displaceable radical and wherein $Z^2$ stands for the hydroxy radical or for a displaceable radical. If $Z^2$ stands for the hydroxy radical, the intermediate compound obtained is further reacted with a reagent which will replace the primary hydroxy radical $Z^2$ with a displaceable radical $Z^1$. The resulting product, which is a compound of the formula:

R—O$CH_2Z^3$ wherein R has the meaning stated above and wherein $Z^3$ stands for the group $$\underset{-CH}{\overset{O}{\diagup\diagdown}}CH_2$$

or the group $$-\overset{OR^5}{\underset{|}{CH}} . CH_2Z^1,$$

wherein $R^5$ and $Z^1$ have the meanings stated above, or which may be, when $R^5$ stands for hydrogen, a mixture of such compounds wherein $Z^3$ has both meanings stated above, is then reacted with an amine of the formula:

$HNR^6$—A—CO—$NR^7$—Y—$R^1$ wherein A, $R^1$, $R^6$, $R^7$ and Y have the meanings stated above, or with a precursor of such an amine.

(b) An oxygenated three-carbon derivative, for example a compound of the formula:

$$\underset{CH_2}{\overset{O}{\diagup\diagdown}}CH . CH_2Z^2 \text{ or } Z^1CH_2 . \overset{OR^5}{\underset{|}{CH}} . CH_2Z^2$$

wherein $R^5$, $Z^1$ and $Z^2$ have the meanings stated above, is reacted with an amine of the formula:

$HNR^6$—A—CO—$NR^7$—Y—$R^1$ wherein A, $R^1$, $R^6$, $R^7$ and Y have the meanings stated above, or with a precursor of such an amine. If $Z^2$ stands for the hydroxy radical the intermediate compound obtained is further reacted with a reagent which will replace the primary hydroxy radical $Z^2$ with a displaceable radical $Z^1$. The resulting product, which is a compound of the formula:

$Z^3CH_2$—$NR^6$—A—CO—$NR^7$—Y—$R^1$ wherein A, $R^1$, $R^6$, $R^7$, Y and $Z^3$ have the meanings stated above, or which may be, when $R^5$ stands for hydrogen, a mixture of such compounds wherein $Z^3$ has both meanings stated above, is then reacted with a phenolic compound of the formula:

R—OH wherein R has the meaning stated above.

A suitable value for $Z^1$, or for $Z^2$ when it stands for a displaceable radical, is, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

A suitable reagent which will replace the primary hydroxy radical $Z^2$ with a displaceable radical $Z^1$ is, for example, a halogenating agent, for example a thionyl halide, for example thionyl chloride or thionyl bromide, or a sulphonylating agent, for example an alkanesulphonyl halide or an arenesulphonyl halide, for example methanesulphonyl chloride, benzenesulphonyl chloride or toluene-p-sulphonyl chloride.

The reaction involving a phenolic reactant may be carried out in the presence of an acid-binding agent, for example an alkali metal hydroxide, for example sodium hydroxide, or an organic base, for example piperidine. Alternatively, an alkali metal derivative of the phenolic reactant, for example the sodium or potassium derivative, may be used as starting material. The reaction may be carried out in a diluent or solvent, for example methanol or ethanol, and it may be accelerated or completed by the application of heat, for example by heating to the boiling point of the diluent or solvent.

The reaction involving an amine of the formula:

$$HNR^6-A-CO-NR^7-Y-R^1$$

may be carried out at ambient temperature or it may be accelerated or completed by the application of heat, for example by heating to a temperature of 90°–110° C.; it may be carried out at atmospheric or at an elevated pressure, for example by heating in a sealed vessel; and it may be carried out in an inert diluent or solvent, for example methanol, ethanol or n-propanol, or an excess of the amine may be used as diluent or solvent.

(c) The series of reactions described under (a) or (b) above may be carried out except that an amine of the formula $R^6NH_2$ is used in place of an amine of the formula:

$$HNR^6-A-CO-NR^7-Y-R^1$$

it being understood that when $R^6$ stands for hydrogen the amine is ammonia. The radical $$-A-CO-NR^7-Y-R^1$$

may then be inserted as a separate step, for example either by the reaction of the final product from the series of reactions described under (a) or (b) above with a compound of the formula:

$$Z^1-A-CO-NR^7-Y-R^1$$

wherein A, $R^1$, $R^7$, Y and $Z^1$ have the meanings stated above, or, when $R^6$ stands for hydrogen, by the reaction under reducing conditions of the final product from the series of reactions described under (a) or (b) above with a carbonyl compound of the formula:

$$A^1-CO-A^2-CO-NR^7-Y-R^1$$

wherein $R^1$, $R^7$ and Y have the meanings stated above and wherein $A^1$ stands for hydrogen or for an alkyl radical and $A^2$ stands for an alkylene radical such that the radical $$\begin{array}{c} A^1 \\ | \\ -CH-A^2- \end{array}$$

has the same meaning as is stated above for A.

The reaction involving a compound of the formula:

$$Z^1-A-CO-NR^7-Y-R^1$$

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or more solvents selected from water, ethanol and an excess of the carbonyl compound used as starting material; or by the presence of an alkali metal borohydride, for example sodium borohydride or lithium cyanoborohydride, in an inert diluent or solvent, for example in one or more solvents selected from water, ethanol, methanol and an excess of the carbonyl compound used as starting material. It is to be understood that when in the starting material $R^1$ stands for an alkenyl radical, or one or more of $R^2$, $R^3$, $R^{12}$ and $R^{13}$ stands for a halogen atom or for a nitro, cyano, alkenyl, alkynyl, alkylthio, alkenyloxy or alkynyloxy radical, or Q stands for an alkenylene radical, or $R^{16}$ stands for an alkenyl or aralkenyl radical, hydrogen and a hydrogenation catalyst are preferably not used to provide the reducing conditions, in order to prevent the radical $R^1$, $R^2$, $R^3$, $R^{12}$, $R^{13}$, $R^{16}$ or Q from being affected by catalytic hydrogenation.

(d) The series of reactions described under (a) or (b) above may be carried out except that an amine of the formula:

$$HNR^6-A-CO-Z^4$$

wherein $R^6$ and A have the meanings stated above, and wherein $Z^4$ stands for a relatively inert substituent, is used in place of an amine of the formula:

$$NHR^6-A-CO-NR^7-Y-R^1$$

or the reaction described under (c) above may be carried out except that the radical $-A-CO-Z^4$ is inserted in place of the radical $-A-CO-NR^7-Y-R^1$.

A suitable value for $Z^4$ is, for example, an alkoxy or aryloxy radical of up to 10 carbon atoms, for example the methoxy, ethoxy or phenoxy radical, or the hydroxy radical.

The resulting product, which has the formula:

$$\begin{array}{c} OR^5 \\ | \\ R-OCH_2.CH.CH_2NR^6-A-COZ^4 \end{array}$$

is either used directly, or is converted into a compound of the formula:

$$\begin{array}{c} OR^5 \\ | \\ R-OCH_2.CH.CH_2NR^6-A-COZ^1 \end{array}$$

wherein R, $R^5$, $R^6$, A and $Z^1$ have the meanings stated above, which is then used to form the amidic linkage $-CO-NR^7-$ by reaction with a compound of the formula $HNR^7-Y-R^1$ wherein $R^1$, $R^7$ and Y have the meanings stated above.

It is to be understood that when $Z^4$ stands for the hydroxy radical the reaction must be carried out in the presence of a condensing agent, for example a carbodiimide.

(e) A compound wherein one or more of $R^5$, $R^6$ and $R^7$ stands for a protecting group may be prepared by the series of reactions described under (a) or (b) or (c) or (d) above. Alternatively, a suitable protecting group may be introduced by conventional means into an intermediate compound at any stage preceding the final stage.

A suitable value for $R^5$ when it stands for a protecting group is, for example, a hydrogenolysable radical, for example an α-arylalkyl, α-arylalkoxy-carbonyl or α-arylalkoxymethyl radical, for example the benzyl, benzyloxycarbonyl or benzyloxymethyl radical or an acyl radical, for example an alkanoyl radical of up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the oxygenated three-carbon radical an acetal radical), for example the tetrahydropyranyl radical, or a tertiary alkyl radical, for example the t-butyl radical.

A suitable value for $R^6$ when it stands for a protecting group is, for example, a hydrogenolysable or tertiary alkyl radical as defined for $R^5$, or a relatively easily hydrolysable acyl radical, for example the 2,2,2-trichloroethoxycarbonyl or t-butoxycarbonyl radical. It is to be understood that when $R^6$ stands for an acyl radical, this radical must be removable under conditions which will not destroy the amidic linkage $-CO-NR^7-$ or the amidic linkage which may be in the substituent $R^4$ or $R^{14}$.

Alternatively, $R^5$ and $R^6$ may be joined together so that one protecting group serves to protect both the oxygen and nitrogen atoms. Such a protecting group may be, for example, a radical of the formula $-CH-R^8-$, wherein $R^8$ stands for hydrogen or for an alkyl radical of up to 4 carbon atoms or an aryl radical of up to 10 carbon atoms, such that it forms, together with the adjacent oxygen and nitrogen atoms and two carbon atoms of the three-carbon radical, an oxazolidine nucleus.

A suitable value for $R^7$ when it stands for a protecting group is, for example, a hydrogenolysable or tertiary alkyl group as defined for $R^5$ or $R^6$.

The hydrogenolysable protecting group $R^5$, $R^6$ or $R^7$ may be removed, for example, by catalytic hydrogenolysis, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The acyl protecting group $R^5$ or $R^6$ may be removed by hydrolysis in the presence of a base, for example an alkali metal hydroxide, in a diluent or solvent, for example water, methanol, ethanol or a mixture thereof. It is to be understood that the hydrolytic conditions used must be sufficiently mild to avoid hydrolysis of the amidic linkage $-CO-NR^7-$ or the amidic linkage which may be present in the substituent $R^4$ or $R^{14}$.

The α-alkoxyalkyl protecting group $R^5$ or the protecting group $-R^8CH-$ formed by $R^5$ and $R^6$ taken together may be removed by hydrolysis in the presence of an acid, for example a mineral acid, for example aqueous hydrochloric acid, and the hydrolysis may be carried out at a temperature of up to 100° C.

The tertiary alkyl protecting group $R^5$, $R^6$ or $R^7$, or the acyl protecting group $R^5$ or $R^6$ when it stands for a tertiary alkoxycarbonyl radical, for example the t-butoxycarbonyl radical, may be removed by treatment with an acid, for example hydrogen chloride, in anhydrous conditions, for example in ethereal solution.

A compound wherein one or more of $R^2$, $R^3$, $R^{12}$ and $R^{13}$ stands for the amino or hydroxy radical may be obtained by the hydrogenolysis of the corresponding compound wherein one or more of $R^2$, $R^3$, $R^{12}$ and $R^{13}$ stands for, respectively, the nitro radical or an α-aralkyloxy radical, for example the benzyloxy radical.

One preferred process for the manufacture of the alkanolamine derivative of the invention comprises the reaction of a compound of the formula:

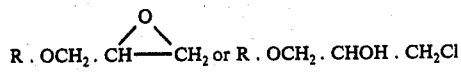

wherein R has the meaning stated above (both of which compounds may be obtained by the reaction of the corresponding phenolic compound with epichlorohydrin), with an amine of the formula $R^6NH-A-CO-NH-Y-R^1$ wherein A, $R^1$ and Y have the meanings stated above and wherein $R^6$ stands for hydrogen or for the benzyl radical, whereafter if $R^6$ stands for the benzyl radical this radical is removed by hydrogenolysis.

A second preferred process for the manufacture of the alkanolamine derivative of the invention comprises the reaction of a compound of the formula:

wherein R has the meaning stated above and wherein $R^6$ stands for hydrogen or for the benzyl radical, with a compound of the formula:

wherein A, $R^1$ and Y have the meanings stated above and wherein $Z^1$ stands for a halogen atom, preferably the chlorine atom, whereafter if $R^6$ stands for the benzyl radical this radical is removed by hydrogenolysis.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be convered into an acid-addition salt thereof by reaction with an acid by conventional means.

As stated above, the alkanolamine derivative of the invention or an acid-addition salt thereof possesses β-adrenergic blocking activity, and furthermore this activity is cardioselective. This activity may be determined by the reversal of isoprenaline-induced tachycardia in rats or cats, a standard test for the determination of β-adrenergic blocking activity, and by relative freedom from antagonism of isoprenaline-induced vasodilatation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is up to twenty times more active as a cardioselective $\beta$-adrenergic blocking agent than practolol. At doses of an alkanolamine derivative of the invention which produce effective $\beta$-adrenergic blockade in rats or cats, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; $\alpha$-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6-8 hourly intervals, or at an intravenous dose of between 1 mg. and 20 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of 1-(2-cyanophenoxy)-3-benzylamino-2-propanol (1.41 g.), $\beta$-chloro-N-(2-furfuryl)propionamide (0.94 g.) and potassium carbonate (0.7 g.) is heated at 90° C. for 18 hours. Water (30 ml.) is added and the mixture is extracted twice with ethyl acetate (30 ml.) each time). The combined extracts are dried and evaporated to dryness, the residue is dissolved in ethanol (50 ml.) and the mixture is shaken with hydrogen in the presence of a 30% palladium-on-charcoal catalyst at laboratory temperature and atmospheric pressure for 4 hours. The mixture is filtered, the filtrate is evaporated to dryness under reduced pressure and the residue is crystallised from ethyl acetate. There is thus obtained 1-(2-cyanophenoxy)-3-$\beta$-(N-2-furfuryl-carbamoyl)ethylamino-2-propanol, m.p. 124°-125° C.

The 1-(2-cyanophenoxy)-3-benzylamino-2-propanol used as starting material may be obtained as follows:

A mixture of 1-(2-cyanophenoxy)-2,3-epoxypropane (17.5 g.) and benzylamine (80 ml.) is kept at laboratory temperature for 18 hours and then evaporated to dryness under reduced pressure. The residue is triturated with water, the mixture is filtered and the solid product is crystallised from isopropanol. There is thus obtained 1-(2-cyanophenoxy)-3-benzylamino-2-propanol, m.p. 78°-79° C.

The process described above is repeated except that $\beta$-chloro-N-(3-pyridylmethyl)propionamide is used in place of $\beta$-chloro-N-(2-furfuryl)propionamide. There is thus obtained 1-2-cyanophenoxy-3-$\beta$-(N-3-pyridylmethylcarbamoyl)ethylamino-2-propanol, m.p. 102°-104° C.

The $\beta$-chloro-N-(3-pyridylmethyl)propionamide used as starting material may be obtained as follows:

3-Chloropropionyl chloride (31.7 g.) is added dropwise during 20 minutes to a stirred, cooled mixture of 3-aminomethyl-pyridine (21.6 g.), sodium bicarbonate (21.0 g.) and water (150 ml.) and the mixture is stirred for a further 1 hour and extracted three times with 100 ml. of ethyl acetate each time. The combined ethyl acetate extracts are dried over anhydrous sodium sulphate and evaporated to dryness under reduced pressure. There is thus obtained, as a gum which is used without further purification, $\beta$-chloro-N-(3-pyridylmethyl)propionamide.

EXAMPLE 2

A mixture of 1-(1,4-benzodioxan-5-yloxy)-2,3-epoxypropane (2.08 g.), $\beta$-benzylamino-N-isopropylpropionamide hydrochloride (2.1 g.), sodium hydrogen carbonate (0.84 g.), water (5 ml.) and isopropanol (40 ml.) is heated under reflux for 4 hours and then evaporated to dryness under reduced pressure. The residue is stirred with water (100 ml.) and the mixture is extracted three times with ethyl acetate (60 ml. each time). The combined extracts are dried and evaporated to dryness, the residue is dissolved in glacial acetic acid (100 ml.) and the solution is shaken with hydrogen in the presence of a 30% palladium-on-charcoal catalyst (0.5 g.) at laboratory temperature and atmospheric pressure until uptake of hydrogen ceases. The mixture is filtered, the filtrate is evaporated to dryness under reduced pressure and the residue is shaken with ethyl acetate (100 ml.) and aqueous N-sodium hydroxide solution (100 ml.). The ethyl acetate layer is separated, washed with water (100 ml.) dried and evaporated to dryness. The residue is crystallised from ethyl acetate and there is thus obtained 1-(1,4-benzodioxan-5-yloxy)-3-$\beta$-(N-isopropylcarbamoyl)ethylamino-2-propanol, m.p. 138°-140° C.

The β-benzylamino-N-isopropylpropionamide hydrochloride used as starting material may be obtained as follows:

A mixture of β-chloro-N-isopropylpropionamide (69.2 g.), benzylamine (53 g.) and n-propanol (500 ml.) is heated under reflux for 18 hours, cooled and filtered. The residue consists of β-benzylamino-N-isopropylpropionamide hydrochloride, m.p. 266°–267° C., and is used without further purification.

In a similar manner to that described above but using a mixture of 1-(benzo[b]furan-4-yloxy)-2,3-epoxypropane (1.9 g.), β-benzylamino-N-benzylpropionamide hydrochloride (3.05 g.), sodium hydrogen carbonate (0.84 g.), water (5 ml.) and isopropanol (40 ml.) there is obtained 1-(benzo[b]furan-4-yloxy)-3-β-(N-benzylcarbamoyl)ethylamino-2-propanol, m.p. 109°–110° C. The β-benzylamino-N-benzylpropionamide hydrochloride used as starting material may also be prepared in the manner described above, m.p. 237°–239° C.

EXAMPLE 3

A mixture of 3-amino-1-phenoxy-2-propanol (1.67 g.) and β-chloro-N-(2-furfuryl)propionamide (0.94 g.) is heated at 90° C. for 4 hours. The mixture is triturated with water (30 ml.) and filtered and the residue is crystallised from toluene. There is thus obtained 1-phenoxy-3-β-(N-2-furfuryl-carbamoyl)ethylamino-2-propanol, m.p. 94°–96° C.

EXAMPLE 4

A mixture of 3-chloro-N-methylbutyramide (1.37 g.) 3-benzylamino-1-phenoxy-2-propanol (5.12 g.) and isopropanol (40 ml.) is heated under reflux for 18 hours. The mixture is cooled and filtered and the filtrate is evaporated to dryness under reduced pressure. The residue is dissolved in 30 ml. of glacial acetic acid and shaken with hydrogen at laboratory temperature and atmospheric pressure in the presence of a 30% palladium-on-charcoal catalyst until 230 ml. of hydrogen are absorbed. The mixture is filtered and the filtrate is evaporated to dryness under reduced pressure. The residue is dissolved in water (50 ml.), washed with ether (50 ml.) and the aqueous phase is treated with aqueous 2N-sodium hydroxide (10 ml.) and the mixture is extracted twice with 50 ml. of chloroform each time. The combined chloroform extracts are dried over anhydrous magnesium sulphate and evaporated to dryness under reduced pressure. A solution of the residue in ethyl acetate (20 ml.) is added to a solution of oxalic acid (1.5 g.) in 50 ml. of ethyl acetate and the mixture is filtered and the residue stirred with water (10 ml.) and filtered. The filtrate is evaporated to dryness and the solid residue is crystallised from acetonitrile. There is thus obtained 1-phenoxy-3-(γ-methylcarbamoylpropyl)amino-2-propanol hydrogen oxalate, m.p. 99°–102° C.

The 3-chloro-N-methylbutyramide used as starting material is prepared by the addition of a 25% solution of methylamine (25 ml.) to a suspension of 3-chlorobutyryl chloride (7.05 g.) in water (25 ml.). The product is extracted with ethyl acetate, dried over anhydrous magnesium sulphate and evaporated to an oil which is used without further purification.

EXAMPLE 5

A mixture of β-alanineamide hydrochloride (0.63 g.), 1-phenoxy-2,3-epoxypropane (0.75 g.), water (15 ml.) and triethylamine (5 ml.) is stirred and heated under reflux for 2 hours. The solution is washed with 25 ml. of ethyl acetate and the aqueous phase is evaporated to dryness under reduced pressure. The residue is chromatographed on silica gel plates (20 cm. × 20 cm. × 2 mm., Merck Kieselgel GF 60F254) using a 180:60:105:30 v/v mixture of toluene, ethyl acetate, ethanol and conc. aqueous ammonia (SG 0.88) as developing solvent, and the band having an $R_f$ value of 0.25 is removed and extracted with hot methanol. The methanol extract is evaporated to dryness under reduced pressure and the residue is dissolved in ethyl acetate and added to a solution of oxalic acid in ether. The mixture is filtered and the residue is crystallised from methanol. There is thus obtained 1-phenoxy-3-β-carbamoylethylamino-2-propanol hydrogen oxalate, m.p. 180°–182° C.

EXAMPLE 6

A mixture of 1-o-methoxyphenoxy-2,3-epoxypropane (0.9 g.), 1.29 g. of β-benzylamino-N-isopropylpropionamide hydrochloride (1.29 g.), isopropanol (40 ml.) and a solution of sodium bicarbonate (0.42 g.) in water (5 ml.) is heated under reflux for 18 hours. The mixture is evaporated to dryness under reduced pressure. The residue is treated with water (20 ml.) and the mixture is extracted twice with ethyl acetate (20 ml.) each time. The combined ethyl acetate extracts are dried over anhydrous sodium sulphate and evaporated to dryness.

The residue is dissolved in 40 ml. of ethanol and shaken with hydrogen at laboratory temperature and atmospheric pressure in the presence of 100 mg. of a 30% palladium-on-charcoal catalyst until 145 ml. of hydrogen have been absorbed and the uptake of hydrogen ceases. The mixture is filtered, the filtrate is evaporated to dryness under reduced pressure and the solid residue is crystallised from ethyl acetate. There is thus obtained 1-o-methoxyphenoxy-3-β-isopropylcarbamoylethylamino-2-propanol, m.p. 115°–117° C.

The process described in the above example is repeated except that the appropriate 2,3-epoxy-1-phenoxypropane and the appropriate β-carbamoylethylamine are used as starting materials, and the hydrogenolysis is carried out in the solvent indicated. There are thus obtained the compounds described in Table I:

Table I

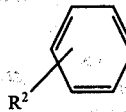

| $R^2$ | n | $YR^1$ | Solvent for hydrogenolysis | m.p. (° C.) | Crystallisation solvent |
| --- | --- | --- | --- | --- | --- |
| 2-cyano | 2 | methyl | ethanol | 118–120 | acetonitrile |
| 2-cyano | 2 | isopropyl | ethanol | 102–104 | ethyl acetate |
| 2-methyl | 2 | isopropyl | ethanol | 109–110 | ethyl acetate |
| hydrogen | 2 | methyl | 10% conc. HCl/ethanol | 91–92 | ethyl acetate |

Table I-continued

| R² | n | YR¹ | Solvent for hydrogenolysis | m.p. (° C.) | Crystallisation solvent |
|---|---|---|---|---|---|
| hydrogen | 2 | isopropyl | 10% conc. HCl/ethanol | (hydrochloride) 129–132 | isopropanol/ ethyl acetate |
| hydrogen | 2 | cyclohexyl | 10% conc. HCl/ethanol | (hydrochloride) 145–147 | isopropanol/ ether |
| hydrogen | 2 | 3-phenoxy-propyl | 10% conc. HCl/ethanol | (hydrochloride) 135–136 | isopropanol |
| hydrogen | 2 | benzyl | glacial acetic acid | 108–110 | ethyl acetate/ petroleum ether (60–80) |
| hydrogen | 3 | benzyl | glacial acetic acid | (hydrochloride) 120–121 | acetonitrile |

The benzylamino-N-alkylpropionamides used as intermediates are prepared according to the method used for β-benzylamino-N-isopropylpropionamide hydrochloride described in Example 2, and they are listed in Table II:

TABLE II

PhCH₂NH(CH₂)ₙCONHYR¹

| n | YR¹ | m.p. (° C.) |
|---|---|---|
| 2 | —Me | 172–174 |
| 2 | —Prˢ | 266–267 |
| 2 | ⟨H⟩ (cyclohexyl) | 260–261 |
| 2 | —CH₂Ph | 239–240 |
| 2 | —(CH₂)₃OPh | 208–210 |
| 3 | —CH₂Ph | 209–210 |

EXAMPLE 7

The process described in Example 2 is repeated except that β-benzylamino-N-benzylpropionamide hydrochloride is used in place of the N-isopropyl derivative. There is thus obtained 1-(1,4-benzodioxan-5-yloxy)-3-β-(N-benzylcarbamoyl)ethylamino-2-propanol, m.p. 104°–106° C.

EXAMPLE 8

The process described in Example 2 is repeated except that 1-(benzo[b]fur-4-yloxy)-2,3-epoxypropane is used in place of 1-(1,4-benzodioxan-5-yloxy)-2,3-epoxypropane. There is thus obtained 1-(2,3-dihydrobenzo[b]fur-4-yloxy)-3-β-(N-isopropylcarbamoyl)ethylamino-2-propanol, m.p. 116°–118° C., the benzofuran ring being partially reduced during the catalytic hydrogenolysis step).

EXAMPLE 9

The process described in Example 3 is repeated except that the appropriate 3-amino-1-aryloxy-2-propanol and the appropriate β-chloro-N-substituted-propionamide are used as starting materials. There are thus obtained the compounds described in the following table:

R—OCH₂.CHOH.CH₂NH(CH₂)₂CONH—Y—R¹

| R | Y | R¹ | m.p.(° C.) | Crystallisation solvent |
|---|---|---|---|---|
| 2-tolyl | CH₂ | 2-furyl | hydrogen oxalate hemihydrate 88–90 | acetonitrile |
| 2-chlorophenyl | CH₂ | 2-furyl | 117–119 | ethyl acetate |
| 2-methoxyphenyl | CH₂ | 2-furyl | 111–112 | ethyl acetate |
| 1-naphthyl | CH₂ | 2-furyl | 120–122 | ethyl acetate |
| phenyl | CH₂ | 3-pyridyl | 94–95 | ethyl acetate |
| 2-chlorophenyl | CH₂ | tetrahydropyran-2-yl | 102–104 | ethyl acetate |
| 2-chlorophenyl | —(CH₂)₂— | 2-pyridyl | 99–100 | ethyl acetate |
| 2-chlorophenyl | CH₂ | 4-pyridyl | 122–123 | ethyl acetate |

EXAMPLE 10

A mixture of β-amino-N-benzylpropionamide (1.78 g.), 1(benzo[b]thien-4 yloxy)-2,3-epoxypropane (2.06 g.) and isopropanol (50 ml.) is heated under reflux for 18 hours and then evaporated to dryness under reduced pressure. The residue is stirred with ethyl acetate (50 ml.) and the mixture is extracted three times with aqueous 2N-hydrochloric acid (25 ml. each time). The ethyl acetate phase is then stirred with aqueous 2N-sodium hydroxide solution, separated, dried over anhydrous magnesium sulphate and evaporated to dryness under reduced pressure. The residue is triturated with dry ether (100 ml.), the mixture is filtered and the solid residue is crystallised from ethyl acetate. There is thus obtained 1-(benzo[b]thien-4-yloxy)-3-β-(N-benzylcarbamoyl)ethylamino-2-propanol, m.p. 109°–111° C.

What we claim is:

1. An alkanolamine derivative selected from the group consisting of a compound of the formula:

R—OCH₂.CHOH.CH₂NH—A—CO—NH—Y—R¹ wherein A is alkylene of up to 12 carbon atoms; wherein Y is a direct link, or alkylene of up to 6 carbon atoms or alkyleneoxy of from 2 to 6 carbon atoms; wherein R is aryl of the formula:

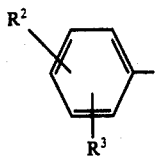

wherein $R^2$ and $R^3$, may be the same or different, each is hydrogen, halogen, hydroxy, amino, nitro, or cyano, alkyl, hydroxyalkyl, cycloalkyl, alkenyl, alkynyl, alkoxy, alkylthio, cycloalkoxy, alkenyloxy, alkynyloxy or alkanoyl each of up to 6 carbon atoms, or aryl, aryloxy or dialkylamino each of up to 12 carbon atoms; or wherein $R^2$ and $R^3$ together form trimethylene, tetramethylene, 1-oxotetramethylene, propenylene, but-2-enylene or buta-1,3-dienylene such that together with the adjacent benzene ring they form respectively indanyl, 5,6,7,8-tetrahydronaphthyl, 5-oxo-5,7,7,8-tetrahydronaphthyl, indenyl, 5,8-dihydronaphthyl or naphthyl; and wherein $R^1$ is furyl or thienyl; and a non-toxic pharmaceutically-acceptable acid-addition salt thereof.

2. An alkanolamine derivative as claimed in claim 1 selected from the group consisting of a compound of the formula given in claim 1 wherein A is ethylene, trimethylene, 1-methylethylene or 1,1-dimethylethylene; wherein $R^2$ is in the 2-position of the phenyl nucleus and is hydrogen, chloro, cyano or alkyl or alkoxy each of up to 3 carbon atoms, and $R^3$ is hydrogen, or R is unsubstituted naphthyl and wherein Y is a direct link, or alkylene of up to 3 carbon atoms or alkyleneoxy of 2 to 4 carbon atoms; and a non-toxic, pharmaceutically-acceptable acid-addition salt thereof.

3. An alkanolamine derivative as claimed in claim 2 wherein A is ethylene, $R^2$ is in the 2-position of the phenyl nucleus and is hydrogen, chloro or cyano, or alkyl or alkoxy each of up to 3 carbon atoms, and $R^3$ is hydrogen, or R is unsubstituted 1-naphthyl; $R^1$ is 2-furyl and Y is methylene, or non-toxic, pharmaceutically-acceptable acid-addition salt thereof.

4. An acid-addition salt as claimed in claim 1 which is a hydrochloride, hydrobromide, phosphate, sulphate, oxalate, lactate, tartrate, acetate, salicylate, citrate, benzoate, β-naphthaoate, adipate or 1,1-methylene-bis-(2-hydroxy-3-naphthoate), or a salt derived from a sulphonated polystyrene resin.

5. The compound 1-phenoxy-, 1-(2-cyanophenoxy)-, 1-(2-chlorophenoxy)-, or 1-(2-methoxyphenoxy)-3-β-(N-2-furfurylcarbamoyl)ethylamino-2-propanol or a non-toxic, pharmaceutically-acceptable acid-addition salt thereof.

6. An alkanolamine derivative as claimed in claim 1, said derivative being 1-2(2-tolyloxy)-3-β-(N-2-furfurylcarbamoyl) ethyl amino-2-propanol or non-toxic, phamaceutically-acceptable acid-addition salt thereof.

* * * * *